(12) United States Patent
Hines

(10) Patent No.: US 8,668,717 B2
(45) Date of Patent: *Mar. 11, 2014

(54) OVER-THE-WIRE EXCLUSION DEVICE AND SYSTEM FOR DELIVERY

(71) Applicant: Electroformed Stents Inc., Stilwell, KS (US)

(72) Inventor: Richard A. Hines, Stilwell, KS (US)

(73) Assignee: Electroformed Stents, Inc., Stilwell, KS (US)

( * ) Notice: Subject to any disclaimer, the term of this patent is extended or adjusted under 35 U.S.C. 154(b) by 18 days.

This patent is subject to a terminal disclaimer.

(21) Appl. No.: 13/741,131

(22) Filed: Jan. 14, 2013

(65) Prior Publication Data

US 2013/0131707 A1 May 23, 2013

Related U.S. Application Data

(63) Continuation of application No. 11/985,021, filed on Nov. 13, 2007, now Pat. No. 8,372,114.

(60) Provisional application No. 60/858,578, filed on Nov. 13, 2006, provisional application No. 60/860,252, filed on Nov. 21, 2006.

(51) Int. Cl.
*A61M 29/02* (2006.01)
*A61B 17/08* (2006.01)
*A61F 2/02* (2006.01)

(52) U.S. Cl.
USPC .......... 606/213; 606/139; 606/151; 606/194; 606/200; 623/23.72

(58) Field of Classification Search
USPC ............... 623/1.1, 1.11, 23.72; 606/139, 151, 606/192, 195, 198, 200, 213; 604/907
See application file for complete search history.

(56) References Cited

U.S. PATENT DOCUMENTS 2,849,002 A * 8/1958 Oddo ............................ 606/192
3,480,017 A * 11/1969 Shute ........................... 606/193
4,364,392 A 12/1982 Strother et al.
4,395,806 A 8/1983 Wonder et al.
4,545,367 A * 10/1985 Tucci ............................ 128/898

(Continued)

OTHER PUBLICATIONS

U.S. Appl. No. 13/741,107, filed Jan. 14, 2013, Hines.

(Continued)

*Primary Examiner* — Corrine M McDermott
*Assistant Examiner* — Mark Mashack
(74) *Attorney, Agent, or Firm* — Fish & Richardson P.C.

(57) ABSTRACT

A modification to allow delivery of a two port medical flow restrictor over a guidewire, and a means to mechanically collapse the new device. A thin walled, foil-like shell, is compacted for delivery. The invention includes the device, delivery assemblies, and methods of placing, and using, the device. A device with an aneurysm lobe and an artery lobe self-aligns its waist at the neck of an aneurysm as the device shell is pressure expanded. Mechanical force collapses both the aneurysm lobe and the artery lobe, captivating the neck of the aneurysm and securing the device. The device works for aneurysms at bifurcations and aneurysms near side-branch arteries. The device, unlike endovascular coiling, excludes the weak neck of the aneurysm from circulation, while leaving the aneurysm relatively empty. Unlike stent-based exclusion, the device does not block perforator arteries. This exclusion device can also limit flow through body lumens or orifices.

12 Claims, 15 Drawing Sheets

(56) References Cited

U.S. PATENT DOCUMENTS

| | | | |
|---|---|---|---|
| 4,836,204 A * | 6/1989 | Landymore et al. | 606/215 |
| 5,002,556 A * | 3/1991 | Ishida et al. | 606/191 |
| 5,065,772 A | 11/1991 | Cox, Jr. | |
| 5,192,301 A | 3/1993 | Kamiya et al. | |
| 5,733,294 A * | 3/1998 | Forber et al. | 606/151 |
| 6,007,573 A | 12/1999 | Wallace et al. | |
| 6,024,756 A | 2/2000 | Huebsch et al. | |
| 6,080,191 A | 6/2000 | Summers | |
| 6,113,609 A * | 9/2000 | Adams | 606/139 |
| 6,168,622 B1 * | 1/2001 | Mazzocchi | 623/1.2 |
| 6,270,515 B1 | 8/2001 | Linden et al. | |
| 6,315,787 B1 * | 11/2001 | Tsugita et al. | 606/213 |
| 6,454,780 B1 * | 9/2002 | Wallace | 606/151 |
| 6,463,317 B1 | 10/2002 | Kucharczyk et al. | |
| 6,506,204 B2 | 1/2003 | Mazzocchi | |
| 6,527,919 B1 | 3/2003 | Roth | |
| 6,547,804 B2 | 4/2003 | Porter et al. | |
| 6,551,303 B1 * | 4/2003 | Van Tassel et al. | 604/508 |
| 6,569,190 B2 | 5/2003 | Whalen, II et al. | |
| 6,669,719 B2 | 12/2003 | Wallace et al. | |
| 6,689,159 B2 | 2/2004 | Lau et al. | |
| 6,855,154 B2 * | 2/2005 | Abdel-Gawwad | 606/200 |
| 6,949,116 B2 | 9/2005 | Solymar et al. | |
| 7,195,636 B2 * | 3/2007 | Avellanet et al. | 606/151 |
| 7,229,454 B2 * | 6/2007 | Tran et al. | 606/157 |
| 7,744,652 B2 * | 6/2010 | Morsi | 623/23.72 |
| 8,372,114 B2 | 2/2013 | Hines | |
| 2002/0082638 A1 | 6/2002 | Porter et al. | |
| 2002/0143349 A1 | 10/2002 | Gifford, III et al. | |
| 2003/0120337 A1 | 6/2003 | Van Tassel et al. | |
| 2003/0181927 A1 | 9/2003 | Wallace | |
| 2004/0034366 A1 * | 2/2004 | van der Burg et al. | 606/119 |
| 2004/0127935 A1 | 7/2004 | VanTassel et al. | |
| 2005/0021016 A1 | 1/2005 | Malecki et al. | |
| 2006/0052816 A1 | 3/2006 | Bates et al. | |
| 2006/0058735 A1 | 3/2006 | Lesh | |
| 2006/0155367 A1 | 7/2006 | Hines | |
| 2006/0167494 A1 | 7/2006 | Suddaby | |
| 2007/0288083 A1 | 12/2007 | Hines | |
| 2009/0281557 A1 * | 11/2009 | Sander et al. | 606/151 |

OTHER PUBLICATIONS

Official Action for U.S. Appl. No. 11/985,021, mailed Sep. 13, 2010, 12 pages.

Official Action for U.S. Appl. No. 11/985,021, mailed Mar. 29, 2011, 11 pages.

Notice of Allowance for U.S. Appl. No. 11/985,021, mailed Oct. 5, 2012, 9 pages.

* cited by examiner

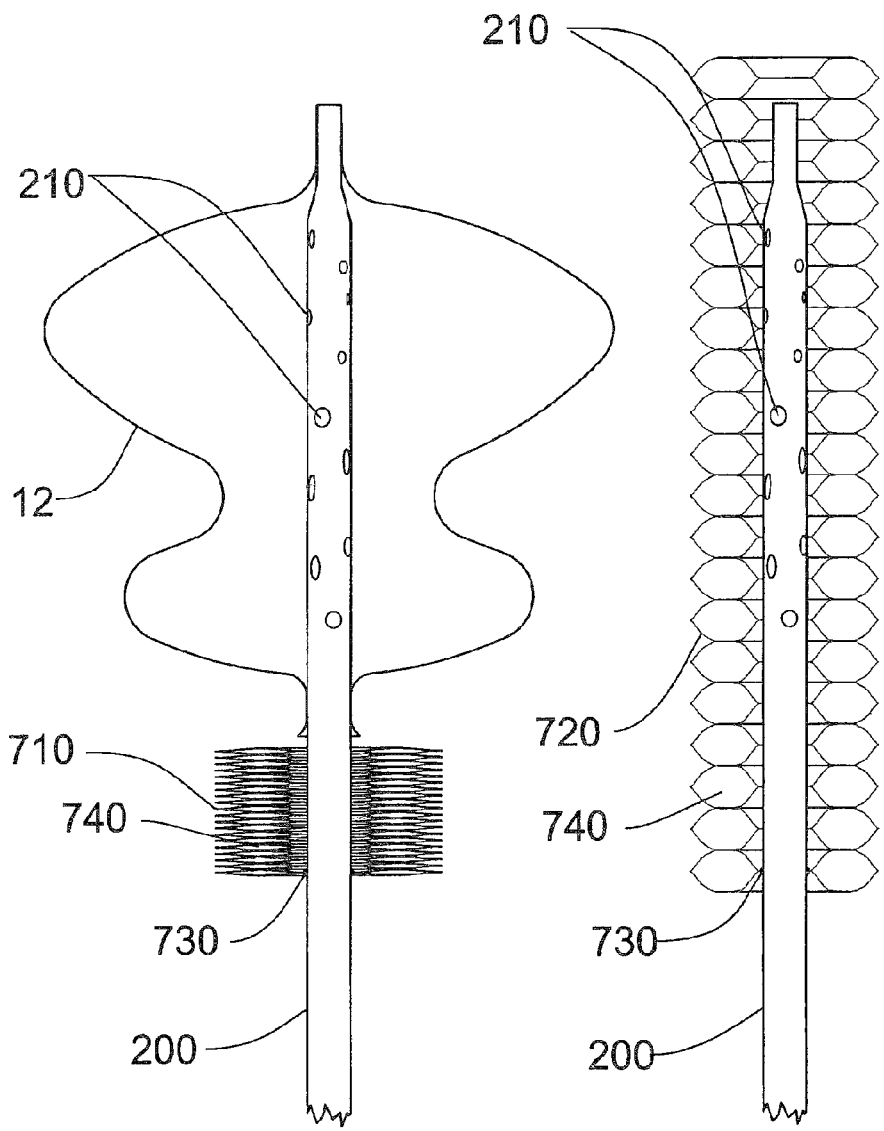

OVER-THE-WIRE EXCLUSION DEVICE AND SYSTEM FOR DELIVERY

CROSS-REFERENCE TO RELATED APPLICATIONS

This application is a continuation of U.S. patent application Ser. No. 11/985,021, filed Nov. 13, 2007, now U.S. Pat. No. 8,372,114, which claims the benefit of priority under 35 U.S.C. §119(e) to U.S. Provisional Patent Application No. 60/858,578, filed Nov. 13, 2006, and to U.S. Provisional Patent Application No. 60/860,252, filed Nov. 21, 2006, each of which are incorporated herein by this reference.

TECHNICAL FIELD

The present invention relates to the field of medical intraluminal delivery of an implantable device that reduces or stops fluid movement that would otherwise flow or circulate through a body lumen or orifice. The invention is well suited for the treatment of neurovascular aneurysms or any other condition that could benefit by completely, or partially, excluding flow through a body orifice or vessel.

BACKGROUND OF THE INVENTION

An aneurysm forms when a dilated portion of an artery is stretched thin from the pressure of the blood. The weakened part of the artery forms a bulge, or a ballooning area, that risks leak or rupture. When a neurovascular aneurysm ruptures, it causes bleeding into the compartment surrounding the brain, the subarachnoid space, causing a subarachnoid hemorrhage. Subarachnoid hemorrhage from a ruptured neurovascular aneurysm can lead to a hemorrhagic stroke, brain damage, and death.

Neurovascular aneurysms occur in two to five percent of the population. It is estimated that as many as 18 million people currently living in the United States will develop a neurovascular aneurysm during their lifetime. Annually, the incidence of subarachnoid hemorrhage in the United States exceeds 30,000 people. Ten to fifteen percent of these patients die before reaching the hospital and over 50 percent die within the first thirty days after rupture. Of those who survive, about half suffer some permanent neurological deficit.

Most unruptured aneurysms are asymptomatic. Some people with unruptured aneurysms experience some or all of the following symptoms: peripheral vision deficits, thinking or processing problems, speech complications, perceptual problems, sudden changes in behavior, loss of balance and coordination, decreased concentration, short-term memory difficulty, and fatigue. Symptoms of a ruptured neurovascular aneurysm include nausea and vomiting, stiff neck or neck pain, blurred or double vision, pain above and behind the eye, dilated pupils, sensitivity to light, and loss of sensation.

Most aneurysms remain undetected until a rupture occurs. Aneurysms, however, may be discovered during routine medical exams or diagnostic procedures for other health problems. Better imaging, combined with the development of improved minimally invasive treatments, will enable physicians to increasingly detect, and treat, more silent aneurysms before problems arise.

Currently, neurovascular aneurysms are treated via a limited range of methods. The potential benefits of current aneurismal treatments often do not outweigh the risks, especially for patients whose remaining life expectancy is less than 20 years.

The original aneurysm treatment, neurosurgical clipping, a highly invasive and risky open surgery, remains the most common treatment for neurovascular aneurysms. Under general anesthesia, a surgeon performs a craniotomy, the removal of a section of the skull, gently retracts the brain to locate the aneurysm, and places a small clip across the base, or neck, of the aneurysm, blocking the normal blood flow from entering the aneurysm. After completely obliterating the aneurysm with the tiny metal clip, the surgeon secures the skull in its original place and closes the wound. The risks of a craniotomy, including the potential for further injury to the brain and additional neurological defect, are exacerbated in patients with a recent brain injury as well as in elderly or medically complicated patients.

In 1995, following the pioneering work of Dr. Fernando Vinuela and Dr. Guido Guglielmi, the FDA approved an endovascular aneurismal treatment: "coiling." In this procedure, an interventional radiologist guides a catheter from the femoral artery, through the aorta, and into the cerebral vasculature, via either the carotid or vertebral artery, until it reaches the aneurysm. Embolic coils, small spring-like devices typically made of platinum, are then threaded through the catheter and packed into the aneurysm until enough coils are present to limit blood flow into the aneurysm. This process, embolization, works by reducing blood circulation in the aneurysm, thereby triggering a thrombus. By converting liquid blood into a solid, coils reduce the danger of the aneurysm leaking or rupturing.

The introduction and continued evolution of the endovascular coiling process has certainly advanced less-invasive aneurismal treatment, but the coiling process has limitations. Strong forces, generated by interluminal flow around and into the aneurysm, often compacts, shifts, or partially dislodges the volume of coils left in the aneurysm. A portion of a coil that prolapses out of the aneurysm neck can lead to serious and adverse consequences (e.g. clot formation, calcification, or other hardening and filling of the artery), and create difficulties in reaching the aneurysm for future treatment.

Recanalization, the reformation of an aneurysm at its neck, occurs in approximately 15 percent of coiled aneurysms and in nearly 50 percent of coiled "giant" aneurysms. Since coiling does not protect the neck of the aneurysm, a coiled aneurysm risks recanalization, which may lead to future rupture and the need for repeat treatment(s). Furthermore, coils create what is known as the mass effect: the permanent lump of coils contained within the aneurysm that maintain an undesirable pressure on the surrounding brain tissue.

The coiling process only works effectively in some aneurysms, specifically small-necked aneurysms where the coils are more likely to stay securely in place within the aneurysm. In wide or medium-necked aneurysms, coils may protrude or prolapse into the parent vessel and create a risk of clot formation and embolism.

In order to combat this design deficit, physicians have begun using stents to improve the effectiveness of coiling. With stent-assisted coiling, a stent lines the arterial wall, creating a screen that secures the coils inside the aneurysm. These stents are generally self-expanding and have a low surface density to make them deliverable. Thus, the stent itself does not limit flow into the aneurysm sufficiently to trigger a thrombus in the aneurysm. However, even these low surface density stents run a significant risk of blocking perforator arteries, creating unpredictable damage to other parts of the brain. Additionally, any stent in the parent artery creates a risk of clot formation in the artery.

To prevent these dangers, the use of an implantable device that covers only the neck of the aneurysm with a greater percent solid area would more effectively restrict blood circulation into the aneurysm, trigger a thrombus (the solidification of liquid blood within the aneurysm), and eliminate the danger of leak or rupture. Ideally, after formation of the thrombus, the aneurismal sac will shrink as the thrombus is absorbed, further reducing the chance of leak or rupture of the aneurysm, while also reducing pressure on the surrounding tissue. Coils or other devices which remain in the aneurysmal sac tend to maintain the original aneurysm volume, and thus the aneurysm continues to exert pressure on the surrounding tissue.

Several additional types of devices designed to limit blood flow into an aneurysm have been described previously, yet none have been commercialized, or approved by the FDA. In these methods, blood flow into the aneurysm is limited to the degree necessary to form a thrombus in the aneurysm without filling the aneurysm with coils, a solidifying agent, or other introduced matter. This type of solution often uses a stent, or stent-like device, in the parent artery. However, unlike stents used to hold coils in place, the surface density of these stents sufficiently limit blood flow into the aneurysm and encourage thrombus formation. For example, U.S. Pat. Nos. 6,527,919; 6,080,191; 6,007,573; and 6,669,719 discuss stents that use methods involving rolled, flat sheets, and U.S. Pat. No. 6,689,159 discusses a radially expandable stent with cylindrical elements where expansion occurs when the stress of compression is removed. Most stents manufactured with a high-percent solid area have limited longitudinal flexibility, tend to have a large delivery diameter, and have an unacceptable probability of blocking perforator arteries, and thus limiting the number of aneurysms they can reach and treat. Additionally, since these methods require a straight parent artery, they will not work at the primary location of most aneurysms: bifurcations, the division of a single artery into two branches. The micro-pleated stent assembly of U.S. Patent Publication No. 2006-0155367 by Hines describes a stent for endovascular treatments that has many advantages over other methods of treating aneurysms. However, this high surface area stent cannot be used to treat aneurysms near side branch or perforator arteries. Even though a micro-pleated, or other neurovascular stent can be patterned with a relatively dense patch area designed to cover the neck of the aneurysm, a micro-pleated stent, or other thin-strutted device that covers artery surface beyond the aneurismal neck, runs a significant, and often unpredictable, risk of restricting blood flow to a smaller, branch artery.

Other methods that artificially solidify aneurysms have been described previously. For example, U.S. Pat. No. 6,569,190 discloses a method for treating aneurysms that fills the aneurismal sac with a non-particulate agent, or fluid, that solidifies in situ. This process leaves an undesirable side effect: a permanent, solidified lump cast in the volume of the aneurysm. The filling agent also risks leaking, or breaking off into, the parent artery, thereby creating a risk of embolus formation.

Previously described methods fill the aneurismal sac with a device or portion of a device. For example, U.S. Patent Publication No. 2006-0052816 by Bates et al., describes a device for treating aneurysms using a basket-like device within the aneurysm that engages the inner surface of the aneurysm and blocks flow into the aneurysm. Similarly, U.S. Pat. No. 6,506,204 by Mazzocchi fills the aneurysm with a wire mesh device that also attempts to captivate the neck of the aneurysm. The devices described by Bates et al., Mazzocchi, and similar devices do not allow the aneurysm volume to shrink and therefore do not lessen pressure on surrounding brain tissue. Such devices depend on an accurate fit within the inner geometry of the aneurismal sac, which is usually quite irregular and difficult to determine, even with advanced imaging techniques. If sized inaccurately, these devices will not completely fill the aneurysm nor seal the neck of the aneurysm, causing recanalization of the aneurysm from the strong lateral forces of the blood. The Mazzocchi device provides no possibility of contouring the part of the device that remains in the parent artery to the arterial wall. Even the smallest amount of material extending into the parent artery runs an unacceptable risk of clot formation and resulting embolism. The Bates et al. device does not adequately protect the aneurysm neck, which may cause an unwanted expansion of the aneurismal neck and sac that risks leak or rupture.

Other devices that bridge the neck of an aneurysm have been described. For example, U.S. Patent Publication No. 2003-0181927 by Wallace describes a neck bridge used to hold an embolic agent within the aneurysm. Wallace makes no provision to captivate the neck of the aneurysm and thus relies on filling the aneurysm with a particulate agent, liquid embolics, or coils in order to secure the device in place. This type of aneurysm treatment does not eliminate the mass effect on surrounding brain tissue. Aneurysm neck bridge solutions described previously, including Wallace, that do not permanently engage the inner surface of the aneurysm must rely on some internal, or external, means in which to hold the neck bridge in its final position. For example, U.S. Patent Publication No. 2006-0167494 by Suddaby attempts to leave some space in the aneurysmal sac that would allow the sac to shrink over time, thereby lessening the mass effect. Suddaby, and similar designs, necessarily rely on an activation mechanism or restraining means to hold the device shape after deployment. Such mechanisms concern physicians for many reasons. Specifically, their size and complexity limits usefulness in the tiny and complex neurovascular anatomy. Additionally, springs or other internal restraining mechanisms risk puncturing the extremely fragile aneurysm neck or sac, which could result in potentially disastrous consequences. Suddaby does not describe, or disclose, any mechanism that holds the device in the described deployed shape, nor does it describe how the device is disconnected from the delivery system. Suddaby fails to provide a workable design, describing a physically impossible transition from an initial delivery shape to a final deployed shape, with no explanation of the mechanisms or forces involved. The need, therefore, remains for an aneurysm exclusion device that can be reliably delivered and deployed to seal the neck of neurovascular aneurysms, in a manner that prevents recanalization of the aneurysm, that eliminates the mass effect, and that poses only a minimal risk of inflicting damage to the aneurismal sac, neck, or parent artery.

Applicant previously disclosed U.S. patent application Ser. No. 11/747,899 EXCLUSION DEVICE AND SYSTEM FOR DELIVERY, which represents the most effective prior art device for sealing the neck of an aneurysm. The present invention modifies the previous device and delivery system to provide for at least greater stability, as well as more effective and consistent, delivery and deployment.

As a result of the previously stated factors, the prior art in the field, including U.S. Ser. No. 11/747,899, have limitations for the treatment of neurovascular and other aneurysms. The present invention, however, overcomes the limitations of these technologies and thereby provides a new hope for the safe, simple, and effective treatment of aneurysms.

BRIEF SUMMARY OF THE INVENTION

This invention details improvements to applicants' previous U.S. patent application Ser. No. 11/747,899 EXCLU- SION DEVICE AND SYSTEM FOR DELIVERY. The current invention details a method to alter the device itself, which enables the herein disclosed delivery and deployment improvements. This invention provides an alternate collapse and disconnect method by adding a second port to the device such that the device can be delivered with a guidewire running through its center. This invention also provides increased stability, deliverability, and deployability, due to its unique two ports, over a guidewire, design. The design facilitates collapse and detachment via the relative movement of two coaxial catheter tubes. One simple movement accomplishes both tasks without the need for additional hardware or complicated thermal or galvanic systems of detachment. The delivery system provides a tubular connection between the aneurismal sac and the outside of the body, allowing the aspiration of blood from the sac and the introduction of therapeutic drugs, devices, or compounds into the sealed sac prior to catheter detachment from the exclusion device. This invention will be referred to herein as the "over-the-wire" exclusion device and endovascular delivery system. The device, when deployed in a lumen or orifice, reduces the flow of fluid past the device. Undesirable device movement due to blood flow during delivery and deployment are far better handled with this over-the-wire version of the exclusion device assembly.

In an illustrative embodiment, the device is delivered endovascularly to the neck of an aneurysm and deployed to block the neck of the aneurysm, thereby reducing blood flow into the aneurysm. The deployment leaves the parent artery fully open and does not block perforator arteries that may exist near the aneurysm. In addition, the present invention treats aneurysms at bifurcations and aneurysms located on the side of an artery.

The exclusion device of the present invention, a thin-walled, ductile shell, transitions between an initial as-manufactured shape, a compacted delivery shape, a pressure expanded shape similar to the as-manufactured shape, a mechanically collapsed shape, and a final balloon-contoured shape. When deployed at the neck of an aneurysm, the exclusion device reduces blood circulation into the aneurysm, triggering a thrombus in the aneurysm that starts the healing process.

The novel double port pressure vessel device is preferably an extremely thin and continuous (other than two ports) ductile shell that includes an aneurysm lobe, a waist, and an artery lobe. The lobe/waist design, the material properties of the device, and the two port over-the-wire design insure that collapse of the device results in the appropriate shape (i.e. the two lobes collapse onto each other and captivate the neck of the aneurysm).

For delivery, the exclusion device is attached in an airtight fashion to the distal end of a pressure tube. The pressure tube, which transmits the necessary pressure to expand the device, may be constructed of any material suitable for advancing the device over a guidewire and through a body lumen to the deployment site and have sufficient tensile strength to shear the distal port from the device to accomplish detachment. Optionally, a thin, tubular protection sheath may cover the device as it is advanced to the deployment site. The protection sheath may be operably extended outside the body so that the sheath may be pulled back, exposing the exclusion device prior to expansion. This release from the outer sheath may occur in controlled stages, allowing the device to be expanded one lobe at a time: the aneurysm (distal) lobe first while the sheath restrains the artery lobe.

After expansion of both the aneurysm and artery lobes, the device is collapsed by applying compressive force generated by decreasing the distance between the distal end of the pressure tube and the distal end of the pusher tube. This force collapses, by plastic deformation, the two lobes, captivating the neck of the aneurysm between the two collapsed lobes.

Disconnection from the delivery catheter is accomplished by continuing the relative movement of the pressure tube and the pusher tube, shearing the distal port of the device shell from the remainder of the shell.

An optional final step in the deployment could use expansions of a balloon catheter, advanced over a guidewire to a point adjacent to the exclusion device. The expanding balloon is used to push any portions of the exclusion device that may be remaining in the artery lumen to the artery wall, completely flattening the artery lobe and proximal stem of the device while fully opening the artery.

Unlike any other devices for blocking the neck of an aneurysm, the over-the-wire exclusion device shell, manufactured according to the preferred embodiment of the present invention, holds its contoured shape without any means of internal or external restraint due to the foil-like nature of its thin and ductile composition.

An exclusion device, manufactured and deployed as described by this invention, may be used to treat a patient with an aneurysm which has a significant leak or which has ruptured completely. The over-the-wire design provides greatly increased stability during delivery and deployment. The present invention provides a treatment option for quickly sealing the neck of an aneurysm in a single step, unlike multiple coil deployments which take much longer. Shorter procedures are always desirable but become crucial when treating stroke caused by a bleeding or ruptured aneurysms. The simplicity, speed, and consistency with which an over-the-wire exclusion device may be deployed make this invention a unique and useful treatment option. The device, once deployed across the neck of a ruptured or leaking aneurysm, provides an immediate barrier to flowing blood, with no need to wait for thrombus formation, as is the case with coiling and non-solid, (e.g. fabric or screen) aneurysm neck sealing devices. A device for use in these urgent cases, with highly dynamic flowing and pulsing blood, must be very stable, easily directed, and reliably deployable, characteristics provided by only the present invention.

The over-the-wire exclusion device and delivery process may be used to close, or block, other body lumens or orifices. For example, the device may be used to close a Patent Foramen Ovale (PFO) or various fistulas. With minor modifications within the scope of this invention, the device may be used to temporarily, or permanently, close fallopian tubes.

Various fabrication and delivery options within the scope of this invention may be used to tailor the device for specific conditions. Overall size of the device, and the relative size and shape of the lobes and waist, may be tailored to fit the treatment of most saccular aneurysms and many other organ or vascular defects.

BRIEF DESCRIPTION OF THE DRAWINGS

FIG. 7 shows a cross-section of an over-the-wire exclusion device mounted on a pressure tube with an expandable bellows used to replace the pusher tube.

FIG. 8 shows the pressure tube with the bellows expanded to collapse and disconnect the exclusion device.

LIST OF REFERENCE NUMERALS

Figure 2:
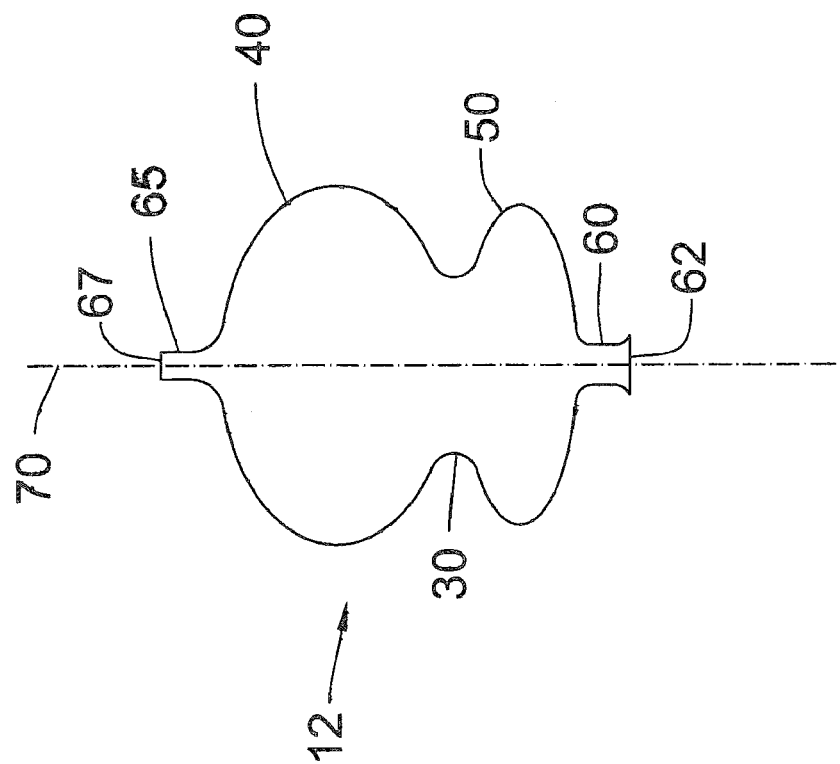
FIG. 2 shows a cross-section of an over-the-wire exclusion device shell.

12 Over-the-guidewire exclusion device
17 Mechanically collapsed over-the-wire exclusion device
20 Mandrel
30 Waist of exclusion device
40 Aneurysm (distal) lobe
50 Artery (proximal) lobe
60 Proximal stem
62 Proximal port
65 Distal stem
67 Distal port
70 Axis of rotation
155 Compacted over-the-wire exclusion device
200 Pressure tube
210 Pressure tube port
212 Drug or other substance
220 Pressure tube/exclusion device glue joint
300 Guidewire
410 Parent artery
420 Smaller arteries distal to a bifurcation
430 Aneurysm
432 Partially collapsed aneurysmal sac
435 Aneurysm neck
500 Pusher tube
600 Balloon catheter
610 Pressure tube hemostasis Y connector
620 Pusher tube hemostasis Y connector
710 Collapsed pusher bellows
720 Expanded pusher bellows
730 Pusher bellows/pressure tube glue joint
740 Inside volume of bellows containing a fluid (gas/liquid) with a boiling point slightly above body temperature

DETAILED DESCRIPTION OF AN ILLUSTRATIVE EMBODIMENT

The current invention provides novel, non-obvious, and greatly useful improvements to applicants' earlier disclosed U.S. patent application Ser. No. 11/747,899 EXCLUSION DEVICE AND SYSTEM FOR DELIVERY. The present invention is a version of the exclusion device, which contains a second port and new delivery and collapse system. The currently disclosed over-the-guidewire exclusion device has many additional inventive features, relative to U.S. patent application Ser. No. 11/747,899, which facilitate mechanical collapse, blood aspiration and or drug introduction, stability upon delivery and deployment, and disconnection from the delivery catheter. The disclosed device is inherently connected with the disclosed novel endovascular delivery and deployment methods. In the illustrative embodiments depicted in FIGS. 1-13, an over-the-wire exclusion device 12 is delivered to an aneurysm 430, positioned at the neck 435 of the aneurysm, pressure expanded, and mechanically collapsed 17, thereby blocking the neck of the aneurysm and reducing blood flow into the aneurysm 430. Unique physical characteristics disclosed herein enable, and result in, a device deployment that leaves all arteries, including the parent (proximal) artery, 410 fully open as no other prior art aneurysm neck barrier device can accomplish.

At a bifurcation, the most common aneurysm location, the proximal artery 410 splits into two smaller arteries 420 as shown in FIGS. 9-13. The deployed exclusion device does not block or in any way impede side branch arteries that may exist near the aneurysm. Aneurysms at bifurcations and aneurysms on the side of an artery may be treated. The exclusion device, deployed to cover the neck 435 of an aneurysm, reduces blood flow into the aneurysm 430 and triggers a thrombus in the aneurysm that starts the healing process.

Figure 1:
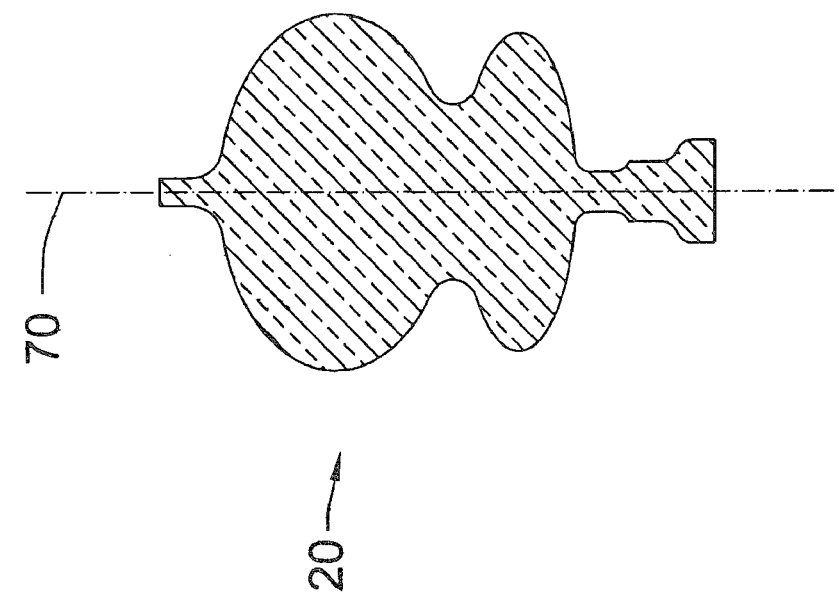
FIG. 1 shows a cross-section of an over-the-wire exclusion device mandrel.
Figure 3:
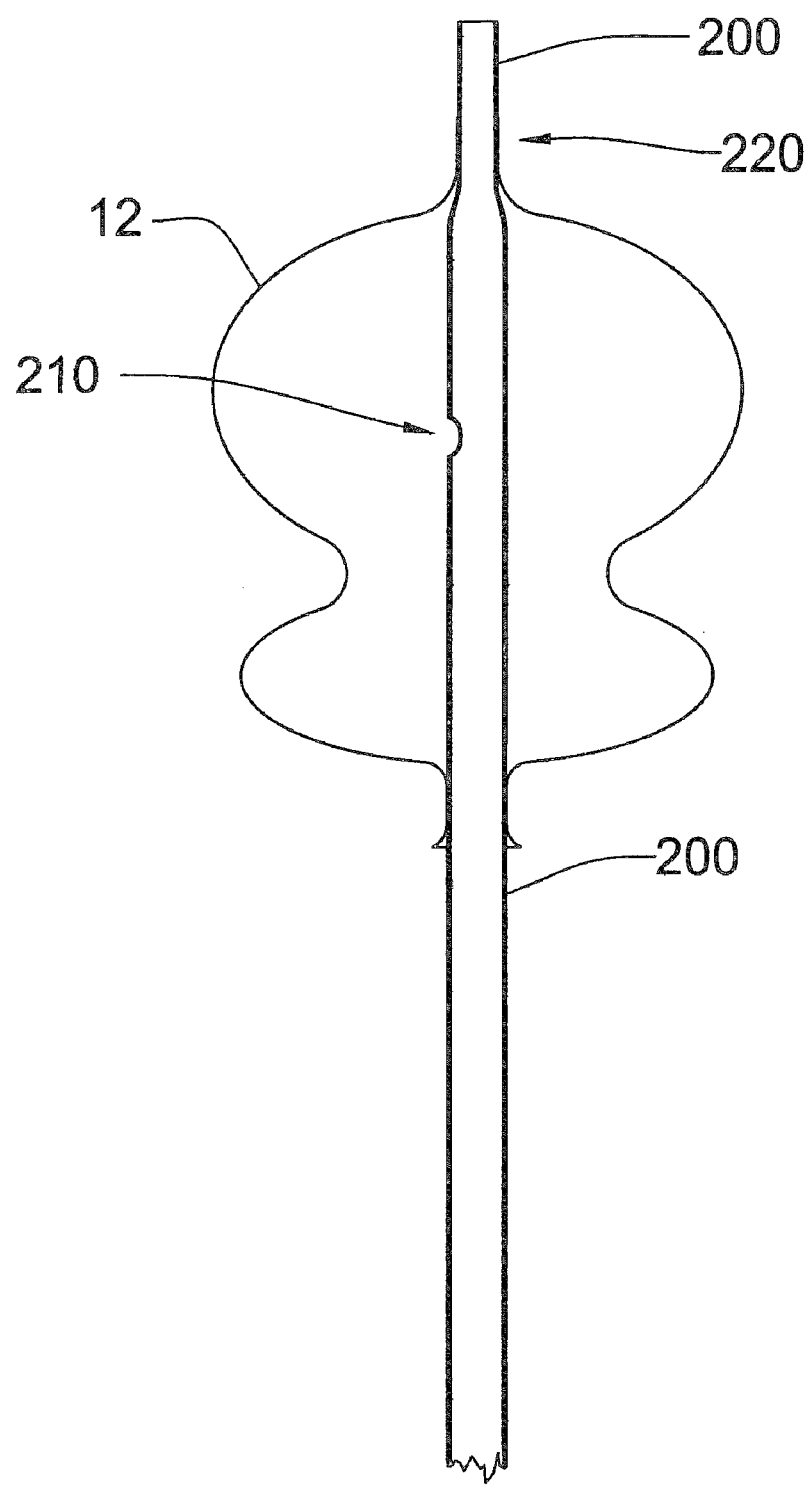
FIG. 3 shows a cross-section of an over-the-wire exclusion device mounted on a pressure tube.
Figure 4:
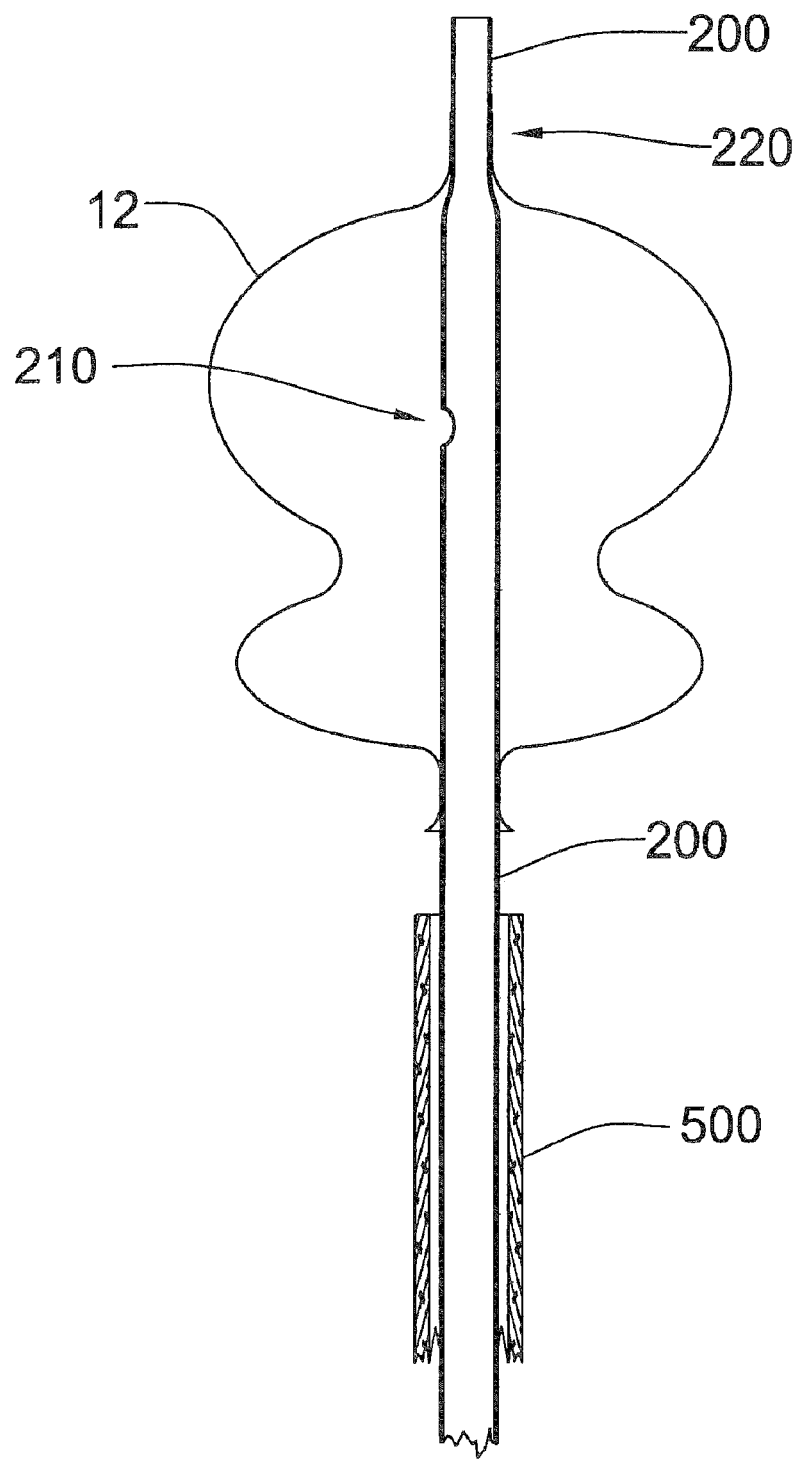
FIG. 4 shows a cross-section of an over-the-wire exclusion device mounted on a pressure tube, with a pusher tube threaded over the pressure tube.
Figure 5:
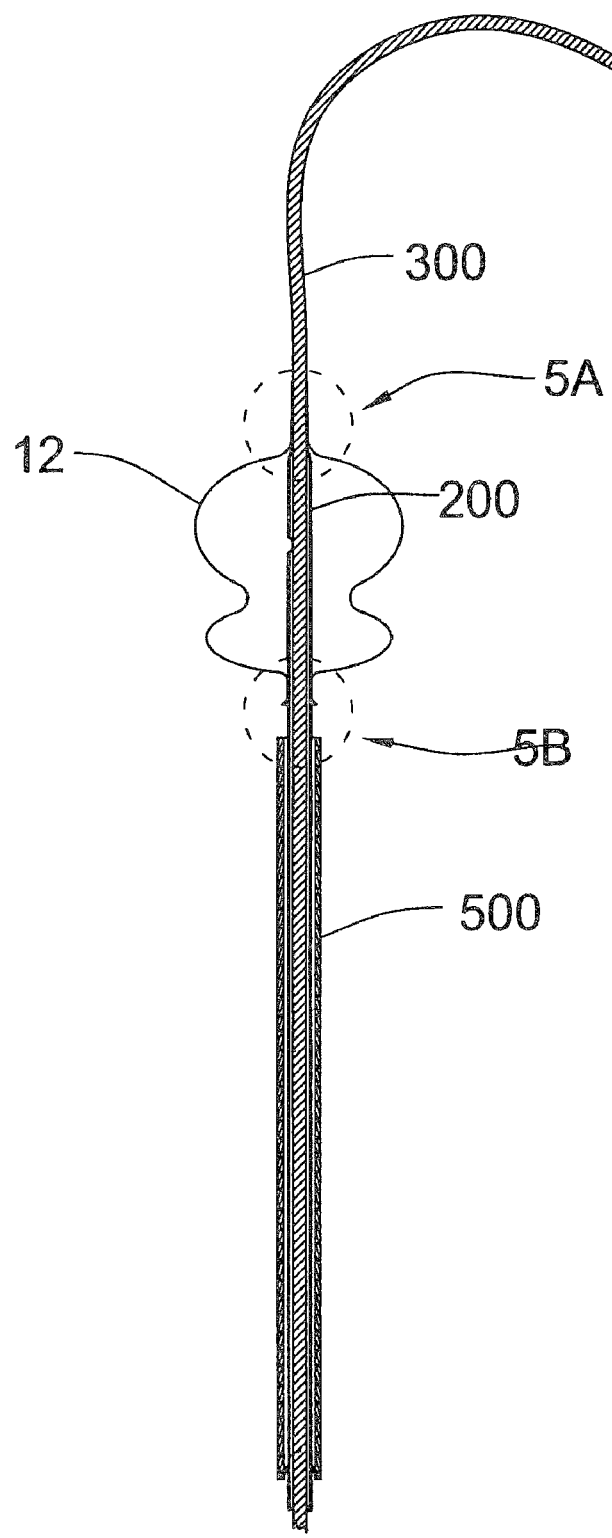
FIG. 5 shows a cross-section of an over-the-wire exclusion device with a guidewire inserted within the pressure tube and through the exclusion device.
Figure 5A:
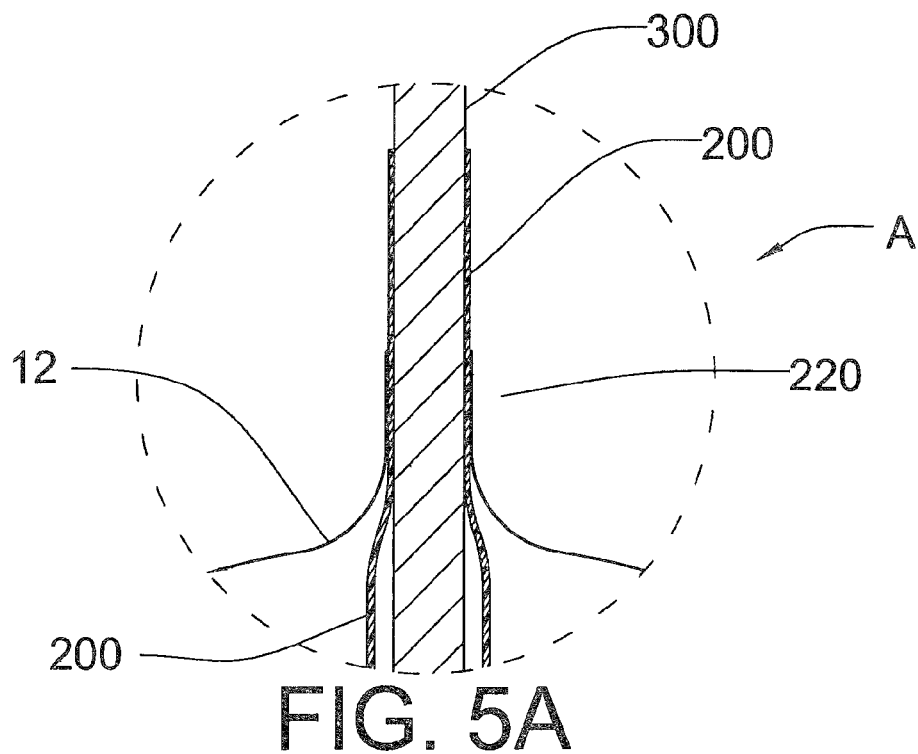
FIG. 5A shows the distal port of an over-the-wire exclusion device, where the device shell is glued to the pressure tube, with a guidewire inside a tapered distal end of a pressure tube, both inside of the device shell distal port.
Figure 5B:
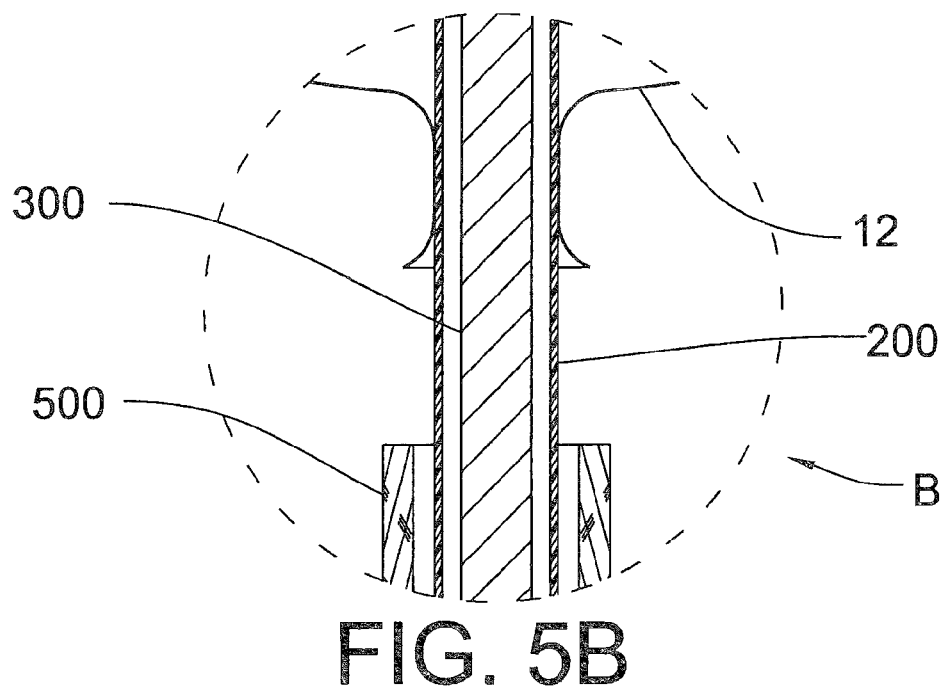
FIG. 5B shows the proximal port of an over-the-wire exclusion device, with a slip fit between the inner diameter of the device proximal port and the pressure tube with the guidewire inside the proximal end of the pressure tube, both inside of the device shell proximal port. The pusher tube is also shown.
Figure 11:
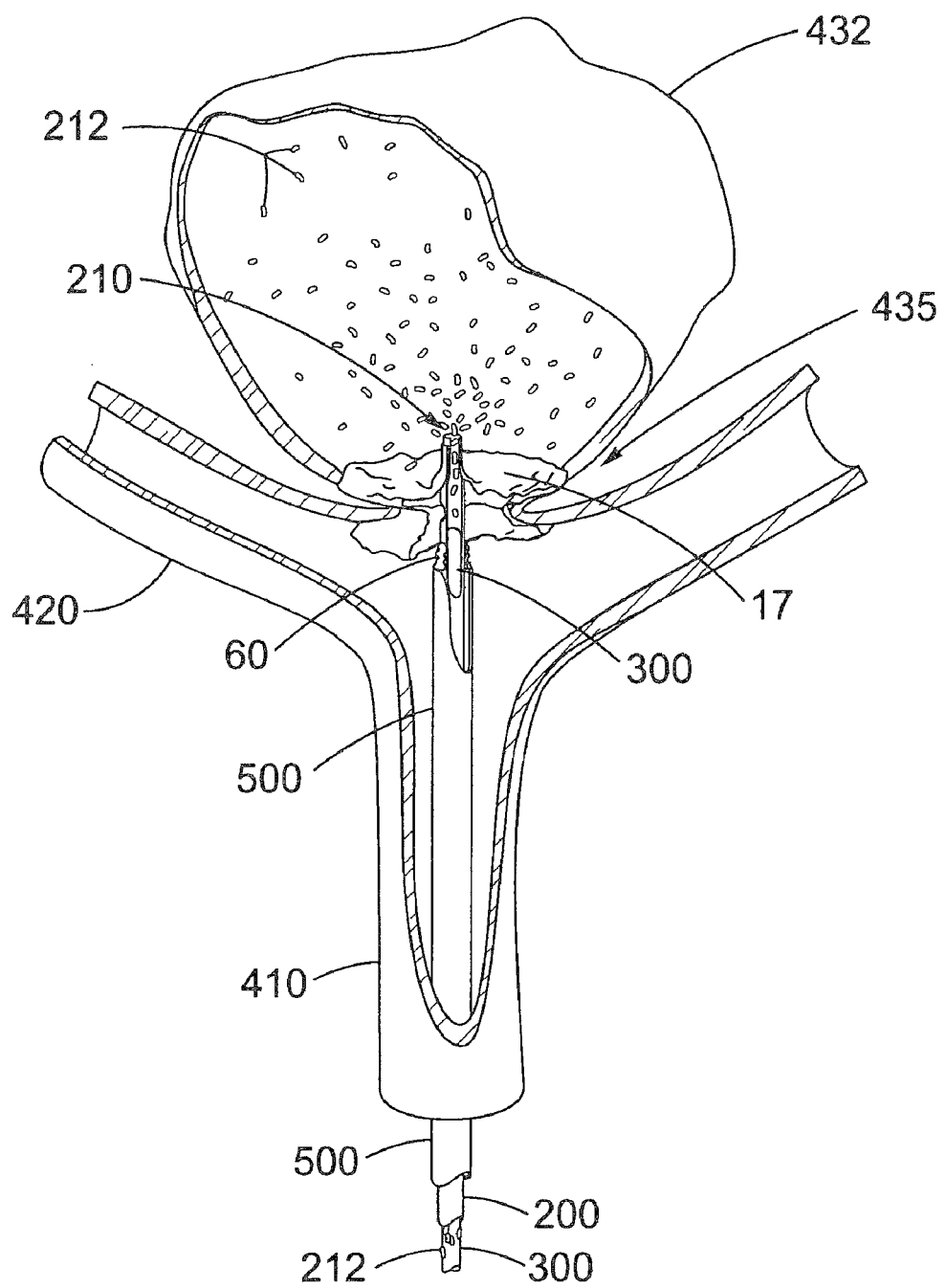
FIG. 11 shows a three-dimensional view of an over-the-wire exclusion device after mechanical collapse, sealing the neck of an aneurysm at a bifurcation. Additionally, blood has been aspirated from the aneurysm and a drug has been injected.
Figure 12:
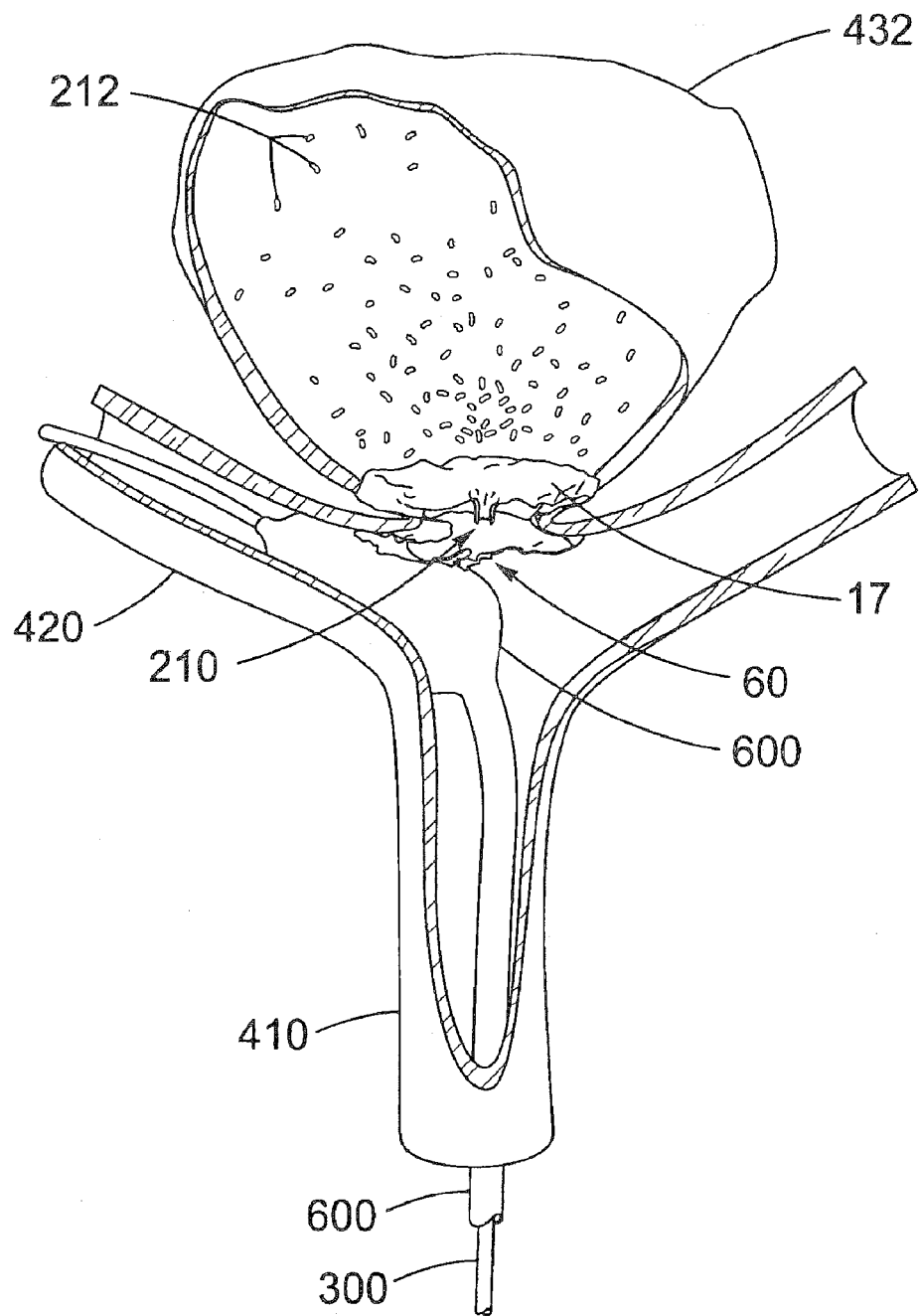
FIG. 12 shows a three-dimensional view of a collapsed over-the-wire exclusion device after disconnection and removal of the delivery catheter and guidewire. Also shown is a balloon catheter used for final contouring.
Figure 13:
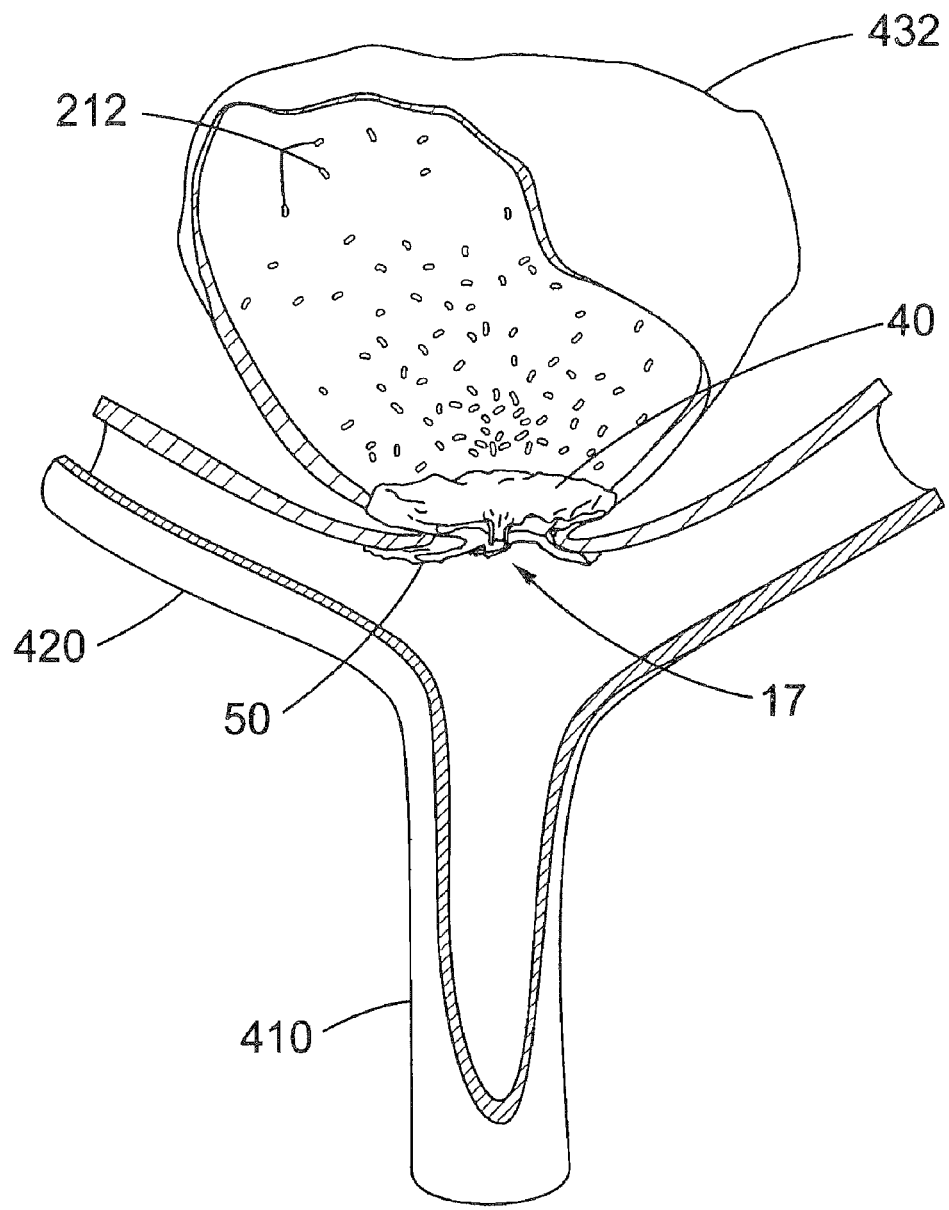
FIG. 13 shows a three-dimensional view of a fully deployed over-the-wire exclusion device.

The over-the-wire device of this preferred embodiment of the invention is a thin-walled, pressure-vessel shell 12, 17, and 155. The device transitions between an initial as manufactured shape, a compacted shape, a pressure expanded shape similar to the as manufactured shape, a mechanically collapsed shape, and a final balloon-contoured shape. The as manufactured shape of the exclusion device 12 is determined by the shape of the sacrificial mandrel 20 as depicted in FIG. 1. The compacted shape will vary slightly depending on the chosen compaction method. Unique device characteristics including ductility, strength, thinness, and geometry, enable an unprecedented compression/expansion ratio. The same characteristics enable unprecedented desirable expansion that is consistent, uniform, controllable, slow, and safe. This invention enables compaction to a small diameter because of the small diameter over-the-wire pressure tube and the small volume required for the compacted thin-walled shell (3 to 8 microns thick in the preferred embodiment). Positive pressure transmitted through a pressure tube 200 expands the device 12, which is itself a pressure vessel, to a shape resembling its as manufactured shape, as is depicted in FIGS. 2-7. Mechanical collapse of the expanded over-the wire device is accomplished by applying compressive force on opposite ends (ports) of the device. This compressive force is generated by decreasing the distance between the distal end of the pressure tube and the distal end of the pusher tube. This force collapses, by plastic deformation, the two lobes, captivating the neck of the aneurysm between the two collapsed lobes, as shown in FIGS. 11-13. A balloon catheter expanded in the parent artery results in a final balloon contoured shape as depicted in FIG. 13.

The pressure tube 200 is designed to accommodate the attachment of the exclusion device shell 12, in an air tight fashion, to its distal end. The ductile pressure-vessel exclusion device shell 12 includes an aneurysm (distal) lobe 40, a waist 30, and an artery lobe 50.

The device 12 requires some form of compaction around the guidewire for delivery. Several compaction methods have been tested and many other possible methods within the scope of this invention exist or will be discovered. The ability of a tightly compacted 155 over-the-wire exclusion device to reform to nearly its manufactured shape 12, due to increased pressure within the nearly air/liquid tight vessel shell, while also having a guidewire and pressure tube through its center, is a very useful and new result. This over-the-wire design enables more effective compaction, while also aiding in consistent and uniform expansion of the device.

For deployment, a guidewire 300 is first advanced until its tip is located in the aneurysm 430. Standard angiographic procedures may be used to view the arteries and aneurysm.

Figure 9:
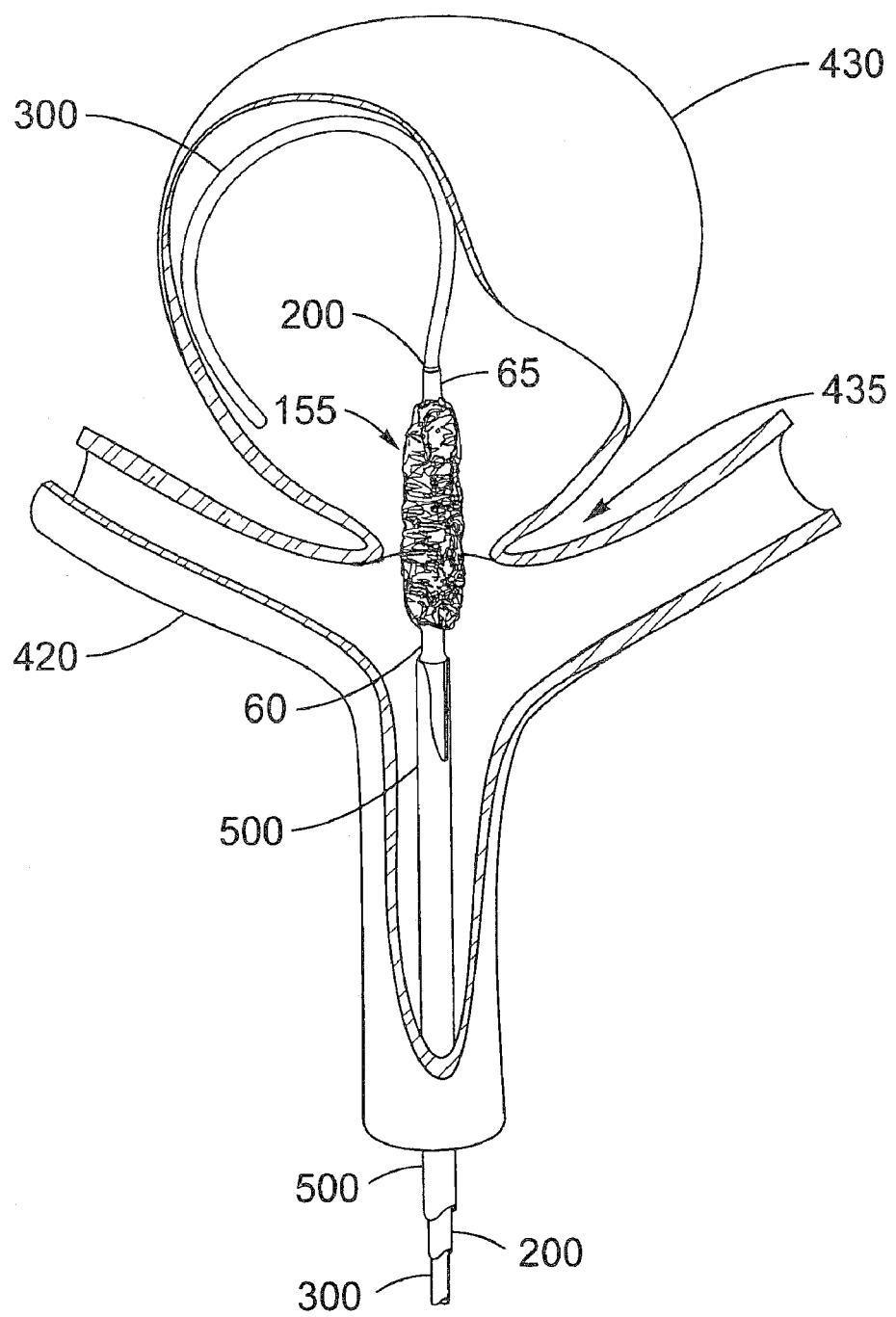
FIG. 9 shows a three-dimensional view of a compacted over-the-wire exclusion device positioned at the neck of an aneurysm at an arterial bifurcation.

After the guidewire is in place, the pressure tube 200 with the compacted device 155 attached to its distal end, is advanced over the guidewire 300, placing the compacted exclusion device 155 at the aneurysm 430, so that the waist of exclusion device is approximately aligned with the neck 435 of the aneurysm, as shown in FIG. 9.

When the device is in position for deployment, the operator may start the expansion of the compacted exclusion device 155 by slowly forcing in contrast or other liquid(s). Minor adjustments in positioning may be made throughout this period of gradual or optionally staged pressure expansion. The position of the device 155 may be adjusted to align the waist 30 of the device with the neck 435 of the aneurysm. Continue to force in contrast or other liquid(s) in order to fully expand the device 155. Existing medical technology allows this liquid pressure application to occur in a regulated manner. A small amount of contrast or other liquid(s) may flow from the distal and proximal ports or through small leaks in the shell without impeding full expansion of the device 17.

It may be advantageous to first apply positive pressure into the exclusion device when only the aneurysm (distal) lobe 40 and waist 30 of the exclusion device are free to expand. This method was described thoroughly by applicant in U.S. patent application Ser. No. 11/747,899. The methods to accomplish staged expansion of the lobes would be similar with the previously disclosed invention and this over-the-wire improvement. Additionally, shell geometry (aneurysm lobe 40 bigger than artery lobe 50) or relative shell thickness (artery lobe 50 thicker than aneurysm lobe 40) could be used to expand the aneurysm lobe 40 first.

An outer sheath may be used to protect the device and the artery during delivery and used to stage the expansion of the lobes of the device. The sheath may be a continuous tube extending from over the compacted device 155 to the outside of the body or a shorter sleeve over the device may be operably pulled back by strings or other mechanical systems. Pulling back the sheath in two steps would allow expansion of the aneurysm lobe first in the aneurysm sac, making it easier to seat the aneurysm lobe 40 at the neck of the aneurysm 430. Next the outer protective sheath would be pulled back to expose the exclusion device artery lobe 50. If necessary, a slight reduction in pressure will facilitate the pull back. With the device properly located at the neck of the aneurysm, the device is fully expanded.

Additionally, the sheath could be pulled back using bellows similar to the bellows shown in FIG. 7 and FIG. 8, except that the glue joint would be on the distal end and the sheath or sheath strings would be attached to the proximal end of the bellows.

Figure 10:
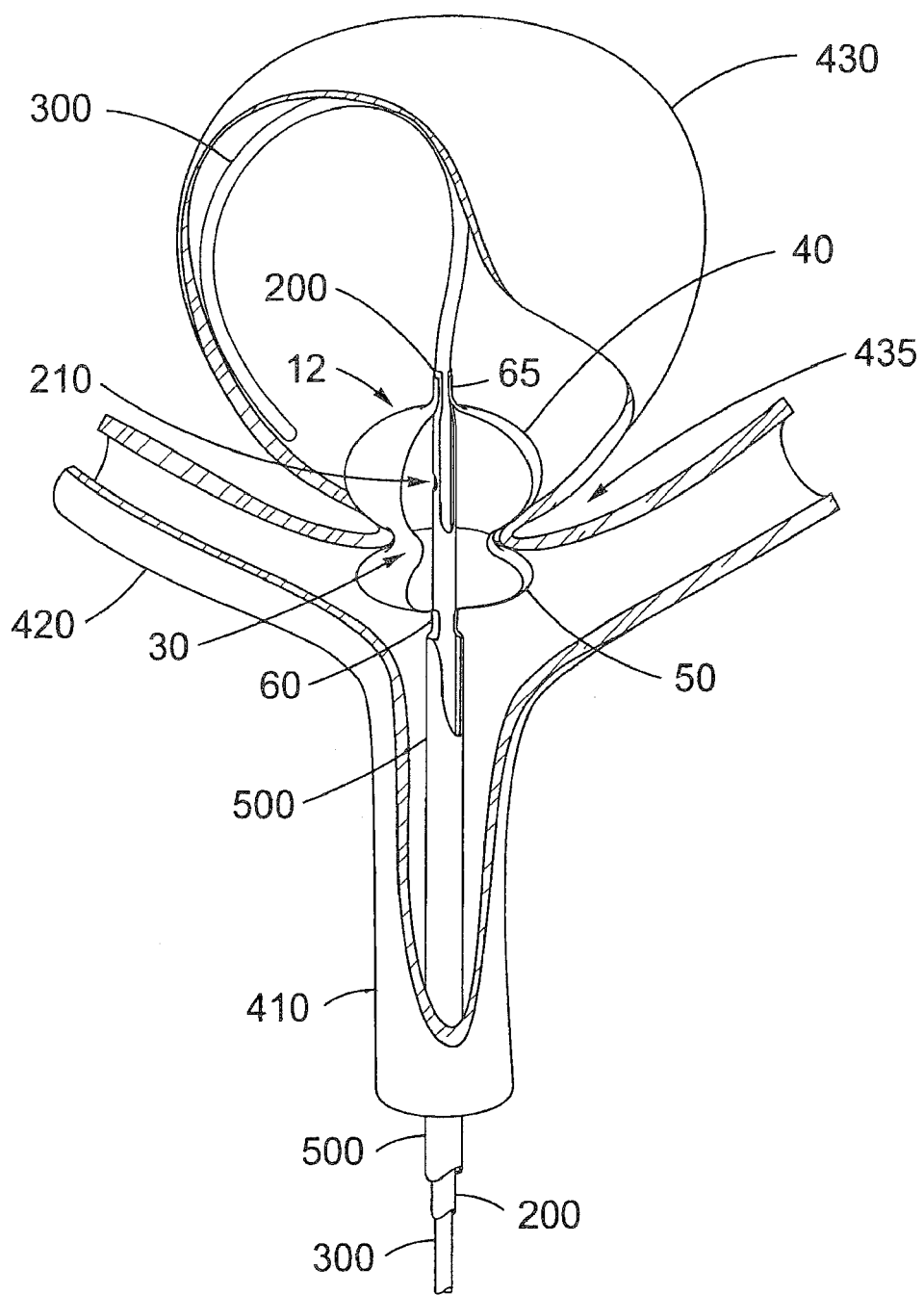
FIG. 10 shows a three-dimensional view of an over-the-wire exclusion device expanded in an aneurysm at a bifurcation.

After the exclusion device is positioned (as shown in FIG. 9) and expanded (as shown in FIG. 10), the device is subsequently collapsed by mechanical forces generated by this the novel collapse method (as shown in FIG. 11), thus captivating the neck 435 of the aneurysm between the two collapsed lobes. To collapse the device, the pressure tube 200 is pulled proximally while the pusher tube 500 is pushed distally.

A unique and useful feature of this invention is that the guidewire 300 may be pulled proximally to locate it inside the pressure tube 200 and open a hydraulic connection to the aneurysmal sac. Optionally, negative pressure may be applied, through the pressure tube conduit in the device, to aspirate blood from the aneurysm 430. Optionally, a therapeutic agent may be injected through the pressure tube 200 into the aneurysmal sac 430. Optionally, an embolic agent may be injected through the pressure tube 200 into the aneurysmal sac 430. Optionally, coils or other devices could be passed through the collapsed exclusion device 17 into the aneurysmal sac 430.

The collapsed exclusion device 17 is preferably detached from the pressure tube 200 by continuing to pull the pressure tube 200 proximally while pushing the pusher tube 500 distally. These two motions are balanced to keep the waist 30 of the device located at the neck of the aneurysm throughout the collapse and disconnection. Disconnection is accomplished by tearing the distal steam of the device from the pressure tube 200.

The pusher tube 200 and pusher tube function could be replaced with a heat operated pusher bellows 710, as shown in FIGS. 7 and 8. The proximal end of the cylindrical bellows would be attached to the pressure tube 200 with glue 730 or other bonding systems. The pusher bellows 710 would contain a small amount of liquid in the internal space 740. The liquid would be selected to have a boiling point slightly above body temperature (37 C). Propanal, dichloromethane, trichlorotrifluoroethane (Freon-113) or many other liquids or mixtures of liquids could be used. While gradually heating the liquid above its boiling point, the bellows would expand and collapse the device 12, and with continued heat input, the bellows would transform to an expanded state 720, as shown in FIG. 8. Such expansion would be sufficient to collapse the device and disconnect the device from the pressure tube 200. Heat could be supplied by an internal heating element or heat could be generated at a conductive loop built into each bellows element and powered by an external electromagnetic field. When energy input is stopped the bellows would cool and thus shorten 710, as shown in FIG. 7. Additional heat operated bellows fixed on their distal end to the pressure tube 200 could be used to pull back the optional protective sheath.

This over-the-wire exclusion device may be disconnected from the pressure tube 200 in a variety of ways, many of which will be, or will become, apparent to those skilled in the art. In addition to the method described above, mechanical, galvanic, thermal, or other methods may be used to detach the device 12 from the pressure tube 200.

After disconnection of the exclusion device, the pressure tube 200 and any remaining hardware are removed from the body.

An optional final step in the deployment (FIG. 12) of the exclusion device advances a low-pressure balloon catheter 600 over the guidewire 300. The balloon at the distal end of the catheter is located, and expanded, contouring any portions of the artery lobe 50 and proximal stem 60 of the collapsed exclusion device 17 against the arterial wall, leaving the lumen fully open. Multiple balloon expansions may be necessary, especially when the aneurysm is located at a bifurcation. FIG. 13 shows a fully deployed device with all delivery and deployment hardware removed.

The following description elucidates, with varied characteristics, the general steps and options, in the design and manufacturing, of exclusion devices and the situations where the present invention may be used.

It is anticipated that a number of shapes, and sizes, of exclusion devices would be manufactured for various applications. The range of types, and shapes, of the exclusion device would be determined by the needs of each particular application. The device may be constructed from rubber, plastic, PARYLENE™, gold, platinum, aluminum, or other ductile metals, singularly, or in combinations.

When using the device to exclude an aneurysm from the circulatory system, the appropriate waist 30 diameter of the exclusion device 12 would be approximately 1 mm smaller than the neck 435 of the aneurysm requiring treatment. The diameters of the two lobes may be approximately 2 mm larger than the neck 435 of the aneurysm. The two lobes need not be symmetrical: each lobe's respective shape, and sizes, is variable and determined by the design, and machining, of an appropriate mandrel.

The proximal stem 60 and distal stem 65 design, and size, are also variable. The proximal port 62 and distal port 67 design, and size, are also variable. In order to facilitate an air tight, and appropriately strong, seal between the pressure tube 200 and the exclusion device distal stem 60, size, including length and diameter, will be based upon the size, and design, of the pressure tube 200.

Electroplating methods were disclosed and discussed in applicants' prior U.S. patent application Ser. No. 11/747,899 and similar methods may be used to produce the device of this invention. Optionally, an over-the-wire device may be manufactured with a thicker wall because the mechanical collapse feature allows the assembly to be designed to provide much more compressive force to collapse the device. A stronger shell may be useful in many situations.

The following delivery assembly design considerations and fabrication steps have been used to build delivery assemblies for animal tests of a preferred embodiment of this over-the-wire exclusion device and assembly.

Figure 6:
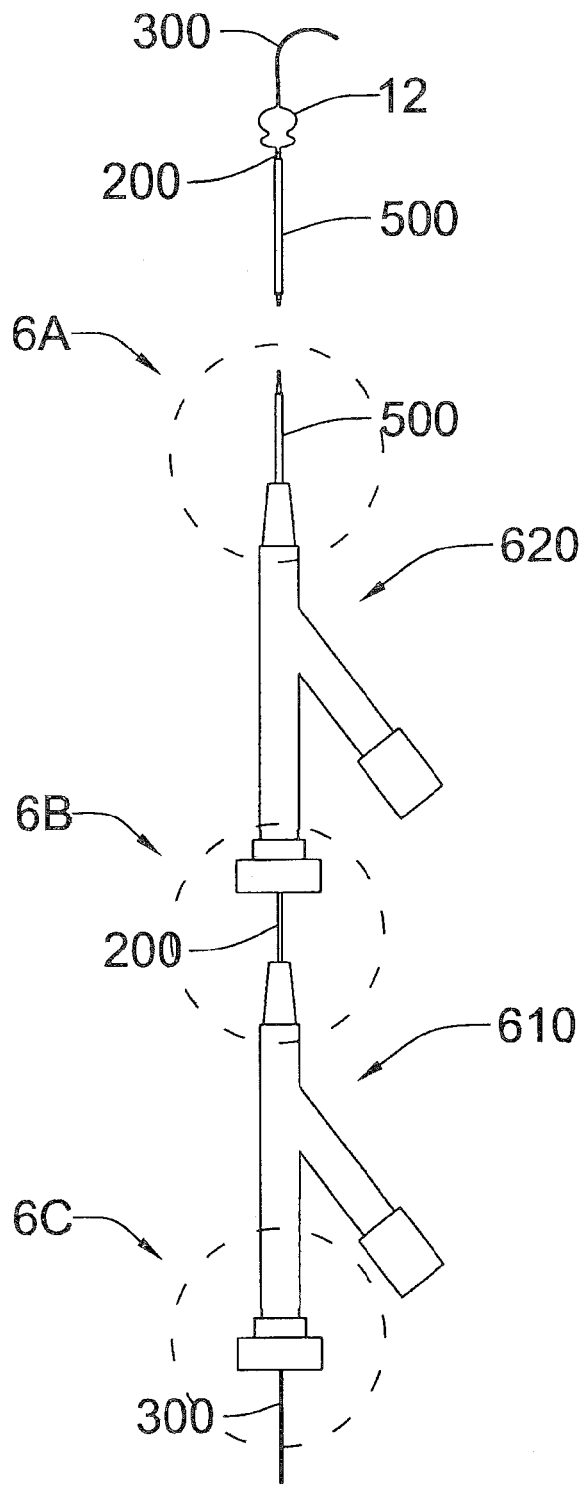
FIG. 6 shows an over-the-wire exclusion device mounted on a pressure tube, attached to a haemostatic Y connector, and a pusher tube attached to a second haemostatic Y connector, with both connectors outside the body, and with a guidewire inserted through the center of the assembly.
Figure 6A:
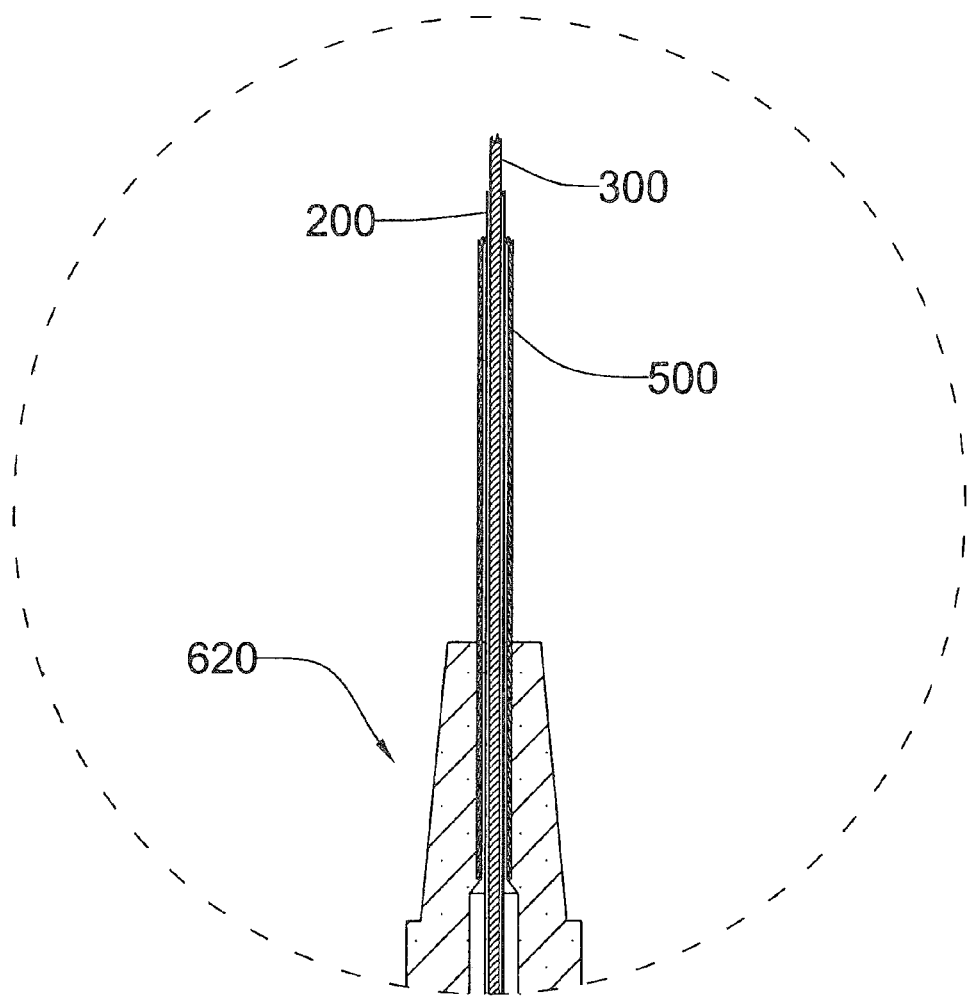
FIG. 6A shows a cross-section of the distal section of the pusher tube hemostasis Y connector.
Figure 6B:
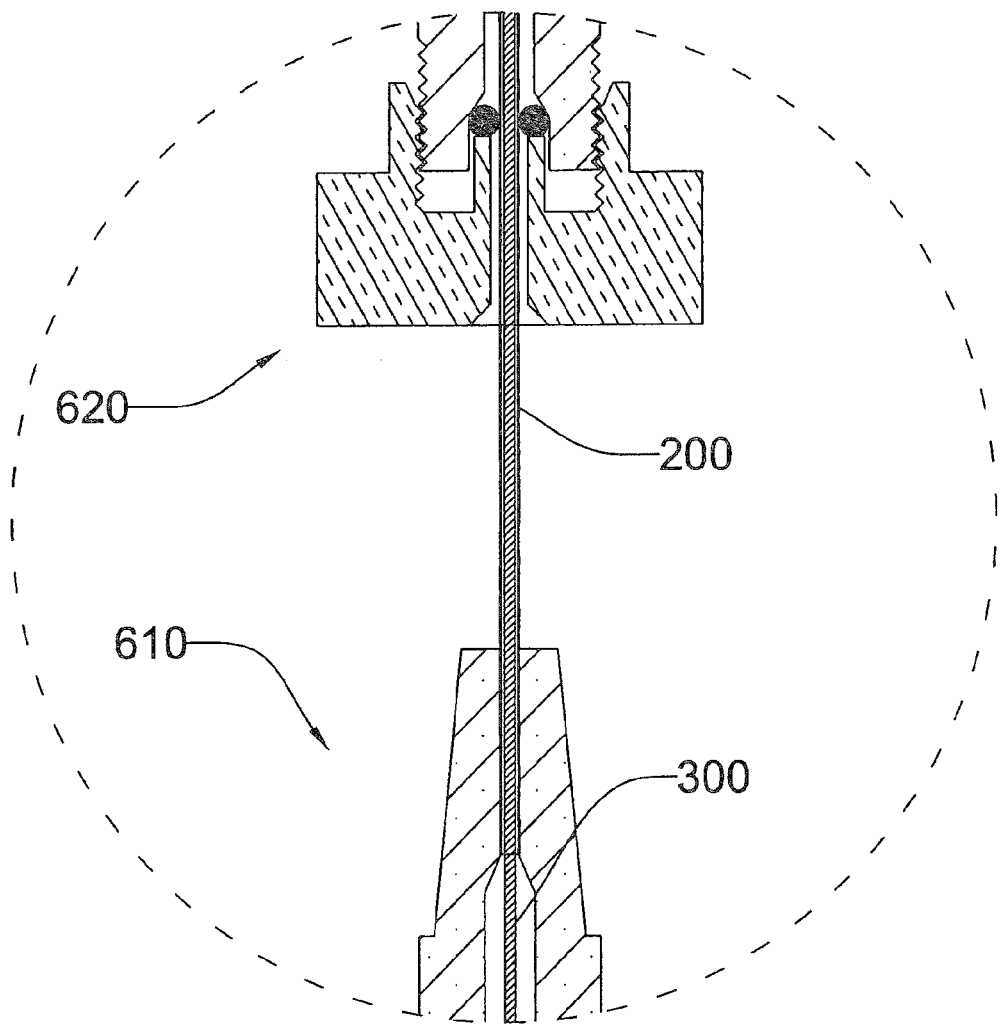
FIG. 6B shows a cross-section of the proximal section of the pressure tube hemostasis Y connector and the distal section of the pusher tube hemostasis Y connector.
Figure 6C:
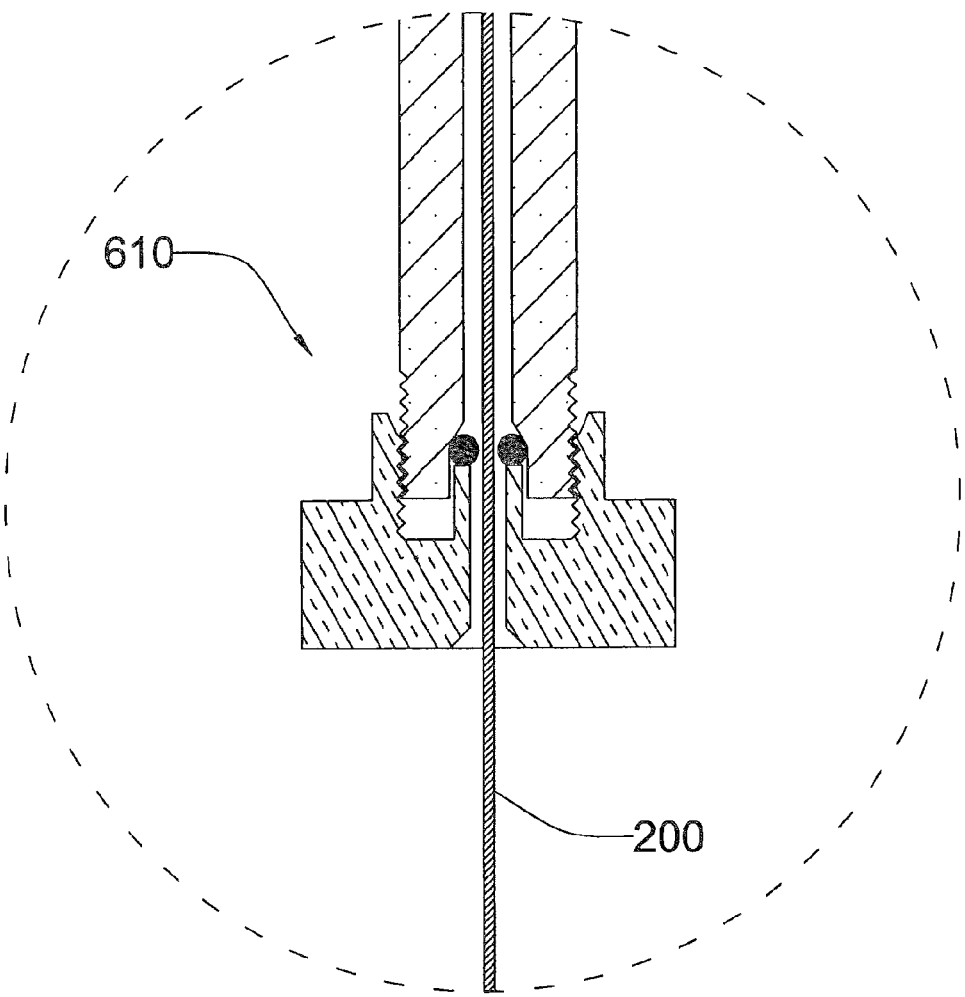
FIG. 6C shows a cross-section of the distal section of the pressure tube hemostasis Y connector.

Delivery assemblies have been built for delivery over a standard 0.014 inch guidewire. Systems could be built around other guidewire sizes. The pressure tube was designed to be strong enough to withstand inflation pressures that could reach 22 ATM (limit of standard balloon inflation syringe pumps) on the proximal end of the pressure tube. The pressure tube 200 also needs to be strong enough in tension to shear the exclusion device 12 from the pressure tube 200. Polyimide is a preferred material for the pressure tube because of its high strength. 0.021 inch ID by 0.024 inch OD tubing has been used for the pressure tube. The distal tip of the tube may be stretched in order to taper it for snug fit on the 0.014 inch guidewire. Tapering has been done by placing a mandrel wire with a diameter slightly larger than the 0.014 inch guidewire e.g., 0.0143 inch inside the polyimide tube. Heat from a ring shaped heating coil heats a short section of the polyimide. After approximately two seconds of exposure to heat the polyimide tube is placed in tension by stretching the tube and drawing its inner diameter down to that of the mandrel wire. The mandrel wire is removed and the tapered section of the tube is cut to a length slightly longer than the length of the distal stem of the exclusion device 12. Hole(s) 210, are then fabricated into the portion of the pressure tube 200 that is contained within the device shell to allow fluid from the pressure tube 200 to pressurize the device for expansion. The hole(s) may be laser drilled, cut with a blade, or any other effective method. An internal mandrel wire about 0.020 inches in diameter may aid in cutting the holes. The polyimide tube is cut to the appropriate length for the desired catheter, (e.g. 100 cm). The proximal end of the pressure tube 200 is attached (FIGS. 6 and 6B) to a Hemostasis high pressure Y connector (Qosina P/N 80358) using a microbore connector (Qosina P/N 62001) and Loctite 4011. The pusher tube 500 has been constructed from thin-wall Teflon tubing. Teflon provides minimal friction with the polyimide and sufficient compression strength to collapse and detach the exclusion device 12. Tightly wound springs made from approximately 0.002 inch diameter Teflon coated wire with an ID of 0.028 inch have also been used to provide a flexible pusher tube with high compression strength and low stored energy prior to excluder detachment. The proximal end of the Teflon pusher tube is attached (FIGS. 6 and 6A) to a Hemostasis Y connector (Qosina P/N 80358) by abrading the surface of the Teflon, treating it with an adhesion promoter (Loctite 770), and bonding it in place with Loctite 4011. The tapered tip of the polyimide tube is threaded through the connector and the Teflon pusher tubing. With the two connectors butted up against each other the Teflon tube is marked for cutting about 4 cm proximal to the tip of the polyamide tube. The Teflon tube is then cut to length. Next, using a 0.014 wire threaded through the polyimide tube as an assembly aid, the device shell is threaded over the 0.014 inch wire and the tapered tip of the polyimide tube until one mm of polyimide tubing extends distally from the distal tip of the exclusion device 12. Loctite 4011 is used to bond the distal tip of the device 12 to the polyimide pressure tube. The proximal port is not bonded, although silicone grease may be applied to reduce leakage. Next, the exclusion device shell 12 is compacted onto the polyimide tube. Any of the other disclosed compaction methods may be used to reduce the crossing profile of the device for delivery by compacting it around a guidewire and pressure tube.

Any combination of biodegradable, dissolvable, or permanent material(s) could be used within the scope of this invention to manufacture the exclusion device.

The exclusion device, and associated assembly, is designed for intraluminal delivery. The design characteristics of the invention allow the exclusion device to be compacted to an exceptionally small size and to be more flexible during, and effective upon, delivery than previously disclosed aneurysm neck-covering devices. In particular, the device may be manufactured, and delivered, as described herein in such a way that enables use in the tiny, tortuous, and complex neurovascular anatomy. The numerous unique benefits, including the degree of safety, accuracy, and reliability in which this over-the-wire exclusion device can be realistically delivered deep into the tortuous arteries of the brain, make it both novel and useful.

The novel device geometry, material properties, and controllable low-pressure inflation-based deployment system, provide self-alignment of the waist of the exclusion device within the neck of the aneurysm (FIG. 10). A standard syringe pump may be used to increase the pressure in the exclusion device. As the device expands, its shape will tend to auto align the waist of the device with the neck of the aneurysm.

Unlike applicants previously disclosed (U.S. patent application Ser. No. 11/747,899) vacuum pressure method for collapsing the device, which can only apply one atm of negative pressure, the over-the-wire version of the invention can develop much larger force to collapse the device. This allows for thicker manufacturing of the device shell (but still very thin compared to Nitinol/fabric composite intraluminal devices), which can be useful for stability and the treatment of large aneurysms or other defects. Mechanical collapse also provides a much more reliable deployment method which also gives the physician more control over the device positioning, collapse, and final placement.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A vascular aneurysm exclusion device comprising:
a shell having a proximal end, a distal end and at least two lobes separated by a waist, wherein the waist is narrower than the at least two lobes, and wherein said shell is capable of containing pressure;
a pressure tube comprising a pressure port near a distal tip thereof and a lumen sized to accept a guidewire therethrough, said distal tip detachably attached to the distal end of said shell, wherein the pressure port communicates pressure to the inside of said shell; and
a pusher slidingly positioned over said pressure tube, the pusher having a distal end placed next to the proximal end of said shell;
wherein the shell is capable of transitioning from a manufactured shape to a compacted shape over said pressure tube; to a pressure-expanded shape resembling said manufactured shape upon application of pressure through said pressure port of said pressure tube; and finally to a mechanically collapsed shape,
wherein the mechanically collapsed shape is formed when the shell is collapsed by a sliding motion of said pusher and said pressure tube causing convergence of the distal end and the proximal end of said shell whereby reducing the at least two lobes to at least two closely-spaced disks.

2. The device as in claim 1, wherein the distal tip of the pressure tube is sized to sealingly fit over the guidewire distally to said pressure port, whereby having the guidewire inside said pressure tube closes off the distal tip of the pressure tube and forms a channel between the guidewire and the lumen of the pressure tube, said channel configured to pressurize said shell from the proximal end of said pressure tube and through said pressure port.

3. The device of claim 1, wherein the shell is formed from a ductile metal capable of maintaining a shape after a shaping force is removed.

4. The device of claim 1, wherein the shell has a thickness of about 3 microns to about 20 microns.

5. The device of claim 1, wherein the shell is formed from an electroformed metal.

6. The device of claim 1, further comprising an electroplated porous layer deposited on an outer surface of the shell.

7. The device of claim 1, wherein the shell further comprises small pores in the range of 5 to 100 microns in diameter.

8. The device of claim 7, wherein the small pores are filled with a material selected from the group consisting of a dissolvable material, a biodegradable material, and combinations thereof.

9. The device of claim 1, wherein the pressure tube communicates pressure between said vascular aneurysm and a proximal end of the pressure tube for removing of fluid from said vascular aneurysm.

10. The device of claim 1, further comprising a material selected from a therapeutic agent, at least one embolic coil, an embolic agent and combinations thereof, wherein the material is injected through the pressure tube into said vascular aneurysm at an endovascular deployment site once the guidewire is removed.

11. The device of claim 1, further comprising a protective sheath to cover said shell in the compacted shape for delivery to an endovascular deployment site.

12. A vascular aneurysm exclusion device comprising:
a hollow shell having a proximal end, a distal end and defining a longitudinal axis between said proximal end and said distal end, said shell capable of containing pressure;
a pressure tube comprising a pressure port near a distal tip thereof and a lumen sized to accept a guidewire therethrough, said distal tip is detachably attached to the distal end of said shell, said pressure tube is slidingly positioned inside the proximal end of said shell, wherein the pressure port is configured to communicate pressure to the inside of said shell; and
a pusher slidingly positioned over said pressure tube, the pusher having a distal end placed next to and sized to abut the proximal end of said shell;
wherein said shell is capable of transitioning from a manufactured shape to a compacted shape to a pressure-expanded shape to a mechanically collapsed shape,
wherein said manufactured shape defines said shell as having two lobes separated by a waist, the waist is narrower than the two lobes,
wherein said compacted shape is formed after said shell is radially compacted towards said longitudinal axis and sized for percutaneous insertion,
wherein said pressure-expanded shape is formed after said shell is expanded from said compacted shape to approximately said manufactured shape, and
wherein said mechanically collapsed shape is formed when said shell is collapsed axially along said longitudinal axis by a sliding motion of said pusher and said pressure tube causing convergence of the distal end and the proximal end of said shell, whereby reducing the two lobes to two closely-spaced disks.

* * * * *